US009021868B2

(12) United States Patent
Sakamoto et al.

(10) Patent No.: US 9,021,868 B2
(45) Date of Patent: May 5, 2015

(54) SENSOR CONTROLLER AND EXHAUST GAS TREATMENT SYSTEM USING THE SAME

(75) Inventors: Yuuki Sakamoto, Kariya (JP);
Mikiyasu Matsuoka, Kariya (JP);
Yuuzou Matsumoto, Kariya (JP)

(73) Assignee: Denso Corporation, Kariya (JP)

( * ) Notice: Subject to any disclaimer, the term of this patent is extended or adjusted under 35 U.S.C. 154(b) by 487 days.

(21) Appl. No.: 13/194,109

(22) Filed: Jul. 29, 2011

(65) Prior Publication Data

US 2012/0031168 A1   Feb. 9, 2012

(30) Foreign Application Priority Data

Aug. 6, 2010   (JP) ................... 2010-177510

(51) Int. Cl.
*G01N 15/06*   (2006.01)
*F01N 11/00*   (2006.01)
*F01N 13/00*   (2010.01)

(52) U.S. Cl.
CPC ............ *F01N 11/00* (2013.01); *G01N 15/0656* (2013.01); *F01N 13/008* (2013.01); *F01N 2550/00* (2013.01); *Y02T 10/47* (2013.01)

(58) Field of Classification Search
USPC ....................................................... 73/61.71
See application file for complete search history.

(56) References Cited

U.S. PATENT DOCUMENTS

| 4,656,832 A | 4/1987 | Yukihisa et al. |
| 8,230,716 B2* | 7/2012 | Nelson et al. .................. 73/1.06 |
| 2002/0060150 A1* | 5/2002 | Hashimoto et al. ........... 204/401 |
| 2010/0147052 A1* | 6/2010 | Nelson et al. ................ 73/28.01 |
| 2011/0048106 A1* | 3/2011 | Zawacki et al. .............. 73/28.01 |

FOREIGN PATENT DOCUMENTS

| JP | 200198931 A * | 4/2001 |
| JP | 2003-185614 | 7/2003 |
| JP | 2006-308440 | 11/2006 |
| JP | 2009-144577 | 7/2009 |

OTHER PUBLICATIONS

Office Action (2 pages) dated Jul. 23, 2013, issued in corresponding Japanese Application No. 2010-177510 and English translation (3 pages).

* cited by examiner

*Primary Examiner* — Laura Martin
*Assistant Examiner* — Alex Devito
(74) *Attorney, Agent, or Firm* — Nixon & Vanderhye P.C.

(57) ABSTRACT

A sensor controller is for a particulate matter detection sensor that includes a pair of opposed electrodes spaced from each other and disposed on an attachment portion. The sensor controller includes a calculation portion configured to calculate an amount of particulate matter attached to the particulate matter detection sensor based on a detection value from the particulate matter detection sensor, and a determination portion configured to determine whether water exists in the exhaust passage based on the detection value. Thus, it is possible to accurately determine whether water exists in the exhaust passage.

9 Claims, 6 Drawing Sheets

SENSOR CONTROLLER AND EXHAUST GAS TREATMENT SYSTEM USING THE SAME

CROSS REFERENCE TO RELATED APPLICATION

This application is based on Japanese Patent Application No. 2010-177510, filed on Aug. 6, 2010, the disclosure of which is incorporated herein by reference.

TECHNICAL FIELD

The present disclosure generally relates to a sensor controller for calculating an amount of particulate matter (PM) based on a detection signal from a particulate matter detection sensor, and an exhaust gas treatment system using the sensor controller.

BACKGROUND

Various types of PM sensors (i.e., particulate matter detection sensors) for detecting the amount of PM exhausted from an engine or the like have been proposed. For example, a PM sensor disclosed in JP-A-59-196453 (corresponding to U.S. Pat. No. 4,656,832) includes a pair of opposed electrodes on an insulating substrate. The accumulation of PM changes a resistance between the pair of the electrodes. By using this property, the PM sensor is configured to detect the amount of PM by measuring the resistance between the electrodes. In such case, a signal output circuit connected to a sensor element is a voltage-dividing circuit formed by a resistance between the pair of opposed electrodes and a predetermined shunt resistance. The signal output circuit is configured to output a voltage at an intermediate point of the voltage-dividing circuit as a sensor detection signal.

In addition, the PM sensor described above has a heating means such as a heater for forcibly burning and removing PM accumulated between the pair of opposed electrodes.

When the engine starts in a low temperature environment for a cold start period, water in the exhaust passage, in which a PM sensor is provided, tends to be attached to the PM sensor and other exhaust sensors. More practically, water formed by a combustion reaction of fuel and air is included in the exhaust gas from the engine, and water contained in the exhaust gas during the cold start period of the engine is cooled in the exhaust passage and condensed. Further, water, generated from the previous engine operation and remaining in the exhaust passage may be scattered and may fall on the sensors. When water falls on or attaches to the PM sensor, resistance between the electrodes changes due to the attached water, and thereby the amount of PM is incorrectly detected in some cases. In addition, an insulating substrate of the PM sensor may be damaged due to a partial cooling of the substrate at water attached portions, when the heater heats the sensor in a water attached state.

SUMMARY OF DISCLOSURE

In view of the above matters, the present invention provides a sensor controller that can accurately detect water in an exhaust passage of an internal combustion engine, and an exhaust gas treatment system having the sensor controller.

According to an aspect of the present invention, a sensor controller to be disposed in an exhaust passage of an internal combustion engine includes: a particulate matter detection sensor that includes a pair of opposed electrodes spaced from each other and disposed on an attachment portion to which conductive particulate matter contained in gas of the exhaust passage is attached, so as to output a detection signal corresponding to a resistance value between the pair of opposed electrodes; a calculation portion configured to calculate an amount of particulate matter attached to the particulate matter detection sensor based on a detection value from the particulate matter detection sensor; and a determination portion configured to determine whether water exists in the exhaust passage based on the detection value.

When the particulate matter detection sensor has PM attached to the attachment portion, the resistance value between the opposed electrodes changes, and the detection value also changes based on the change of the resistance value. In the sensor controller, change of the resistance value due to the attachment of water on the attachment portion is utilized, for the detection of water in the exhaust passage based on the detection value from the particulate matter detection sensor. Thus, it is possible to predict behaviors of the detection value at a time of water attachment, For example, an actual detection value and a signal output range at a water attachment state are compared with each other, thereby accurately determining whether water exists on the attachment portion.

BRIEF DESCRIPTION OF THE DRAWINGS

Objects, features, and advantages of the present disclosure will become more apparent from the following detailed description made with reference to the accompanying drawings, in which.

DETAILED DESCRIPTION

Figure 1:
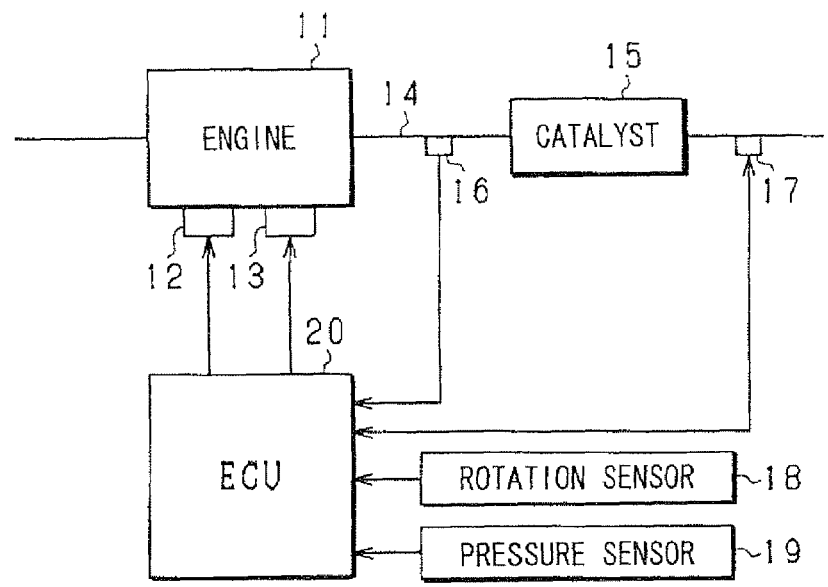
FIG. 1 is a block configuration diagram of an engine control system in an embodiment of the present disclosure.

Hereinafter, embodiments of the present invention will be described on the basis of the drawings. In this embodiment, a vehicle engine system with a vehicle-mounted engine is provided to monitor the amount of PM (amount of conductive particulate matter) of exhaust gas exhausted from an engine. In particular, a PM sensor is provided in an engine exhaust pipe. Based on the amount of attached PM detected by the PM sensor, the amount of PM is monitored. FIG. 1 shows a configuration diagram of the outline of the system.

In FIG. 1, an engine 11 is a direct fuel-injection gasoline engine. The engine 11 is provided with a fuel injection valve 12 and an igniter 13 which serve as an actuator for the operation of the engine 11. An exhaust pipe 14 of the engine 11 is provided with a three-way catalyst 15 serving as an exhaust gas purification system. An A/F sensor 16 is provided at an upstream side of the three-way catalyst 15, and a PM sensor 17 as a particulate matter detection sensor is provided at a downstream side of the three way catalyst 15. The A/F sensor 16 is a heater-equipped exhaust sensor, and a sensor element in the A/F sensor 16 is heated to a certain activation temperature by the electric supply to the heater. The system is further provided with a rotation sensor 18 for detecting an engine rotation speed, a pressure sensor 19 for detecting the pressure of an intake pipe, and the like.

An ECU 20 includes a microcomputer constructed of a well-known CPU, ROM, RAM, and the like as its main component. The ECU 20 executes various control programs stored in the ROM to perform various control processes of the engine 11, based on the operating state of the engine 11. That is, the ECU 20 receives input of respective signals from the above sensors or the like, and controls the operation of the fuel injection valve 12 and the igniter 13 by computing the amount of injected fuel or the ignition timing based on the received signals. Regarding the fuel injection control, the detection value of the A/F sensor 16 is used to perform the air-fuel ratio feedback control.

The ECU 20 calculates the amount of PM actually exhausted from the engine 11 (actual PM emission amount) based on a detection signal from the PM sensor 17, and performs a diagnosis of the combustion state of the engine 11 based on the actual PM emission amount. Specifically, when the actual PM emission amount exceeds a predetermined value for determination of abnormality, it is determined that the amount of exhausted PM is excessive and that the engine abnormality is being caused.

Further, the ECU 20 may variably control the control state of the engine 11 based on the actual PM emission amount calculated from the detection result of the PM sensor 17. For example, the ECU 20 can control the amount of injected fuel, the injection timing of fuel, and the ignition timing, based on the actual PM emission amount.

Figure 2:
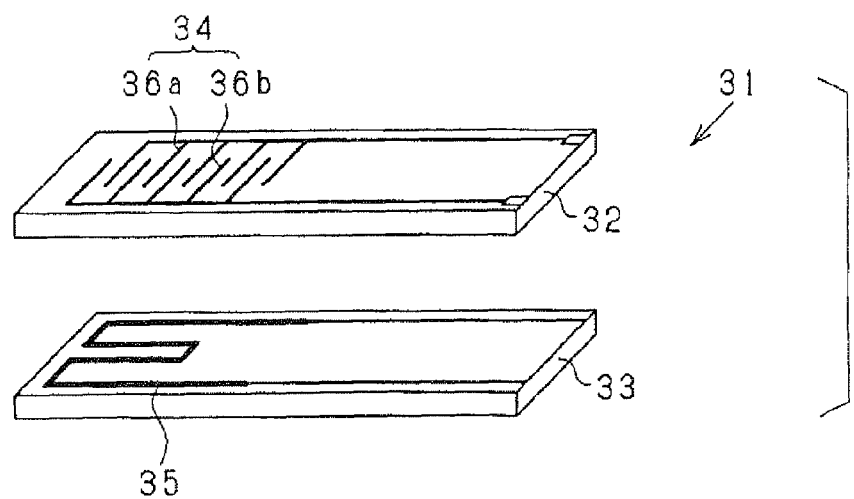
FIG. 2 is an exploded perspective view of a sensor element in the embodiment of the present disclosure.
Figure 3:
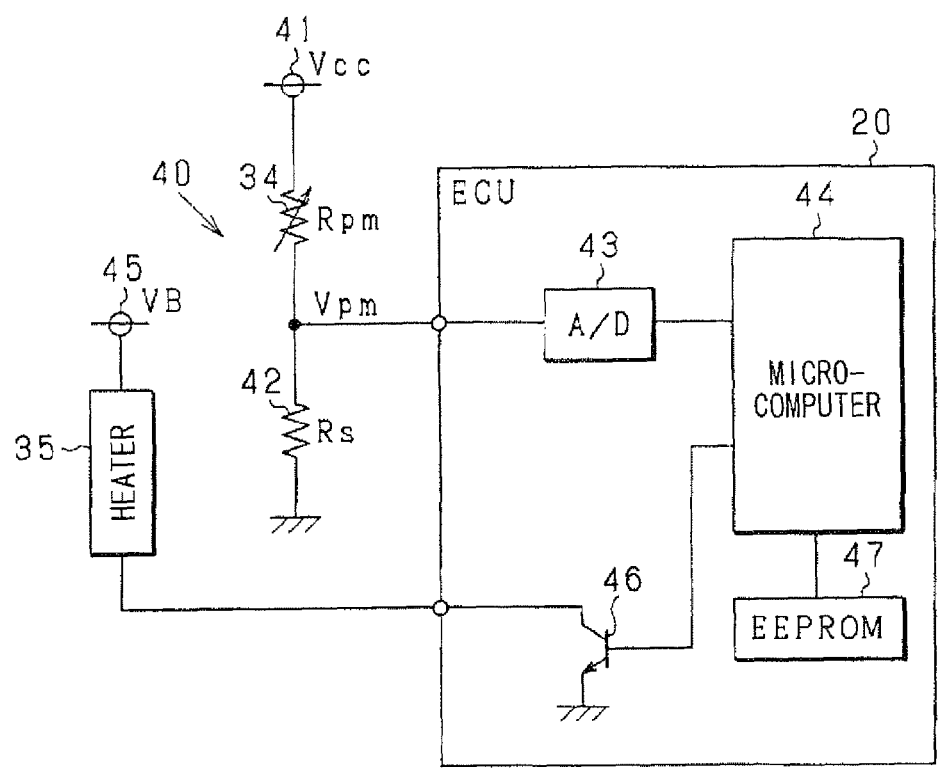
FIG. 3 is a schematic view of a particulate matter (PM) sensor in the embodiment of the present disclosure.

Next, the structure of the PM sensor 17, and the electric configuration of the PM sensor 17 will be described with reference to FIGS. 2 and 3. FIG. 2 shows an exploded perspective view of the main structure of a sensor element 31 in the PM sensor 17, and FIG. 3 shows an electric configuration diagram regarding the PM sensor 17.

As shown in FIG. 2, the sensor element 31 includes two pieces of insulating substrates 32 and 33 each having a longitudinal plate shape. One insulating substrate 32 is provided with a PM detector 34 for detecting the amount of PM. The other insulating substrate 33 is provided with a heater 35 for heating the sensor element 31. The sensor element 31 has a lamination structure in which two layers of the insulating substrates 32 and 33 are stacked with each other. The insulating substrate 32 corresponds to an attachment portion.

A pair of detection electrodes 36a and 36b are provided on a surface of the insulating substrate 32 opposite to the other insulating substrate 33, and the electrodes 36a and 36b are spaced apart from each other. The PM detector 34 is made from this pair of the detection electrodes 36a and 36b. Each of the detection electrodes 36a and 36b has a comb-like shape with teeth. The teeth of the combs of the detection electrodes 36a and 36b are alternatively arranged to be opposite to each other at predetermined intervals. The heater 35 includes a heating element made of, for example, an electrically-heated wire.

The shape of the pair of the detection electrodes 36a and 36b is not necessarily limited to the above-mentioned one, and may be a curved one. Alternatively, the detection electrodes 36a and 36b may be formed from a pair of electrode portions, each of which is formed of one wire and which are arranged opposite to each other in parallel, while being spaced apart by a predetermined distance.

Although not shown in the illustration, the PM sensor 17 includes a holder for holding the sensor element 31. The sensor element 31 is fixed to an exhaust pipe with one end held by the holder. In such case, a part including at least the PM detector 34 and the heater 35 is positioned in the exhaust pipe, while the PM sensor 17 is attached to the exhaust pipe with the insulating substrate 32 (i.e., PM attachment portion) of the sensor element 31 directed toward the upstream side of the exhaust gas. Thus, when exhaust gas containing PM flows through the exhaust pipe, the PM is attached and accumulated onto the detection electrodes 36a and 36b and its surroundings over the insulating substrate 32. The PM sensor 17 has a protective cover for covering protrusion parts of the sensor element 31.

When PM in the exhaust gas is attached and accumulated onto the insulating substrate 32 of the sensor element 31, the PM sensor 17 having the above structure detects the amount of PM based on a change in resistance of the PM detector 34 (that is, resistance value between the pair of detection electrodes 36a and 36b) which corresponds to the amount of accumulated PM.

As shown in FIG. 3, the PM sensor 17 has the following electric configuration. That is, the PM detector 34 of the PM sensor 17 has one end thereof connected to a sensor power supply 41, and the other end thereof connected to a shunt resistor 42. The sensor power supply 41 is constructed of, for example, a constant-voltage circuit. The constant voltage Vcc is 5 V, for example. In such case, the PM detector 34 and the shunt resistor 42 form a voltage-dividing circuit 40, in which a voltage of an intermediate point is input as a PM detection voltage Vpm (sensor detection value) to the ECU 20. That is, in the PM detector 34, the resistance Rpm changes according to the amount of accumulated PM. The PM detection voltage Vpm is changed by the resistance Rpm and the resistance Rs of the shunt resistor 42. Then, the PM detection voltage Vpm is input to a microcomputer 44 via an ND converter 43.

When Vcc=5 V, and Rs=100 kΩ, the PM detection voltage Vpm can be determined by the following equation (1):

$$Vpm = 5\,V \times 100\,k\Omega / (100\,k\Omega - Rpm) \qquad (1)$$

In the above equation, when the amount of accumulated PM is 0 (i.e., substantially equal to 0), the resistance Rpm of the PM detector 34 becomes infinite, thereby resulting in Vpm=0 V. When the resistance Rpm of the PM detector 34 decreases to, for example, 1 kΩ due to the accumulation of PM, the PM detection voltage Vpm becomes Vpm=4.95 V. In this way, the PM detection voltage Vpm changes according to the amount of accumulated PM on the PM detector 34. The microcomputer 44 calculates the amount of accumulated PM according to the PM detection voltage Vpm.

The voltage-dividing circuit 40 forms a signal output circuit. The PM detection voltage Vpm is variably changed by the voltage-dividing circuit 40 in an output range of 0 to 5 V. In such case, the maximum output value of the PM detection voltage Vpm is about 5 V, or, more strictly, a value that is slightly lower than 5 V.

Further, a heater power supply 45 is connected to the heater 35 of the PM sensor 17. The heater power supply 45 is, for example, an in-vehicle battery, and electricity supply to the heater 35 from the in-vehicle battery heats the heater 35. In such case, a transistor 46 as a switching element is connected to a low side of the heater 35, and heating control of the heater 35 is performed by switching on/off of the transistor 46 under control of the microcomputer 44.

When the energization of the heater 35 is started with the PM accumulated on the insulating substrate 32, the temperature of the accumulated PM increases, thereby forcibly burning the accumulated PM. Such forcible burning of the PM burns and removes PM accumulated on the insulating substrate 32. For example, at the start of the engine 11, at the end of the operation of the engine 11, or when the amount of accumulated PM is determined to reach a predetermined amount, or when the amount of total engine operation time or vehicle travel distance reaches a certain threshold value, the microcomputer 44 determines that a request for forcible burning of the PM is made, and thus controls the heating operation of the heater 35.

Further, the ECU 20 is provided with an EEPROM 47 serving as a memory for a backup to store therein various types of studied values, abnormality diagnosis values (diagnosis data, or diag-data) or the like.

In case of a cold start period of the engine 11, an inside of the exhaust pipe 14 is in a low temperature state, and the low temperature of the exhaust pipe 14 cools the exhaust gas from the combustion of the engine 11, thereby causing vapor contained in the exhaust gas to be condensed and attached to the sensor element 31 (i.e., to the insulating substrate 32) of the PM sensor 17. Further, water remaining in the exhaust pipe 14 from the previous operation of the engine 11 may be scattered by the gas flow in the pipe 14 due to the operation of the engine 11, and may be attached to the sensor element 31 (i.e., on the insulating substrate 32).

In the PM sensor 17, a pair of detection electrodes 36a, 36b may become conductive with each other due to the scattered water when water is attached to the insulating substrate 32. Therefore, there may be a possibility that the amount of PM is incorrectly detected. Further, there may be a possibility that damage of the sensor element 31 is caused during a forcible burning of PM at the engine start time, due to the attachment of condensed/scattered water on the sensor element 31 in the low temperature environment. For example, partial cooling of the element 31 may be caused by the attached water during the heating by the electricity supply to the heater 35.

Therefore, by using the PM detection voltage Vpm that has respectively different values when the insulating substrate 32 has the attached water and when the insulating substrate 32 has no water attached thereto, water attachment to the PM sensor 17 is determined. In such determination, if the PM sensor 17 has water attached thereon, it is determined that water exists in the exhaust pipe 14, and, based on a determination result of the water attachment, a control based on the PM detection voltage Vpm may be restricted, and/or forcible burning of the PM accumulated on the insulating substrate 32 may be restricted.

Further, when the PM detector 34 is in a PM accumulated state at an engine start time, it cannot be determined, in some cases, whether the PM detection voltage Vpm is caused by the accumulated PM or is caused by the water attachment. Therefore, in the present embodiment, the PM detection voltage Vpm is acquired as the stop time detection value at the time of stopping of the engine, and the PM detection voltage Vpm is also acquired as the start time detection value at the start period of predetermined time length subsequent to the previous stopping of the internal combustion engine. Thus, it is possible to perform the water attachment determination of the PM sensor 17 based on the result of comparison between the stop time detection value and the start time detection value.

According to the water attachment determination based on the PM detection voltage Vpm, it can be determined that water has disappeared from the PM detecting element 34 after the attachment thereto. That is, in other words, the water attachment to the insulating substrate 32 is temporary, and water on the insulating substrate 32 vaporizes as the engine 11 warms up and the temperature in the exhaust pipe 14 goes up. Therefore, when the sensor element 31 is in a water attached state, the PM detection voltage Vpm has a relatively great value, and the voltage value Vpm decreases to correctly reflect the amount of PM accumulation on the insulating substrate 32 as water on the insulating substrate 32 vaporizes. Therefore, by utilizing the above behavior of the change of the PM detection voltage Vpm, disappearance of water from the PM sensor 17 during the start period of the engine 11 can be determined. In other words, it can determine whether water in the exhaust passage has disappeared in this manner. Here, the water disappearance includes the water non-existence due to water evaporation, water movement with the flow of the exhaust gas, water-removing or the like.

Figure 4:
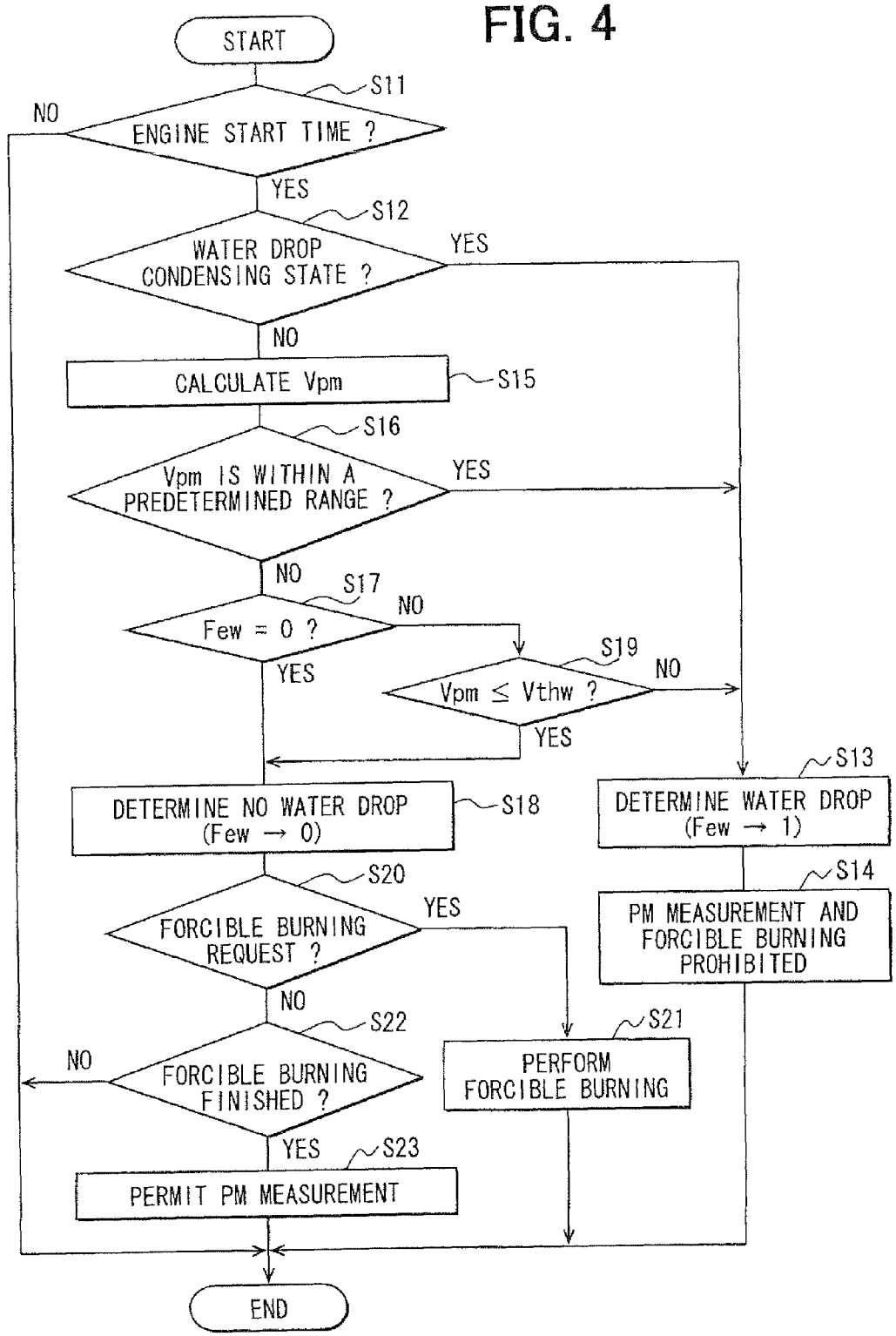
FIG. 4 is a flowchart of a water attachment determination process in the embodiment of the present disclosure.

Then, the water attachment determination of the PM sensor 17 is explained in the following in a more practical manner. FIG. 4 shows a flowchart of a water attachment determination process in the embodiment, and this process is repeated at regular intervals by the microcomputer 44.

In FIG. 4, it is determined whether the engine operation is in a predetermined engine start period at the time of starting the engine 11 in step S11. For example, a time period from a start of the engine 11 (i.e., turning on of the ignition) to an end of warm-up of the engine 11 is defined as the engine start period. Alternatively, a time period from a start of the engine 11 to an increase of engine coolant temperature to a warmed-up value (e.g., 80° C.) may be defined as the engine start period.

If the engine operation is not in the engine start period, the present process is ended without performing the water attachment determination process of the PM sensor 17. On the other hand, if it is determined that the engine operation is in the engine start period, the control process proceeds to step S12, and it is determined whether the exhaust pipe 14 is in a water drop condensing state. In the present embodiment, an exhaust temperature sensor is arranged near the PM sensor 17, and exhaust temperature is detected, and pressure in the exhaust pipe 14 is compared with a saturated steam pressure at the detected exhaust temperature. If the current saturated steam pressure at the detected exhaust temperature is lower than the internal pressure of the exhaust pipe 14, the exhaust pipe 14 is in a state that easily condenses water drop, and it is determined that the water attachment to the PM sensor 17 is possible to be caused. Further, the exhaust temperature may be calculated based on a heater resistance value of the PM sensor 17, for example. The heater resistance value is calculated based on detection of the heater resistance voltage (i.e., a battery voltage) and a heater electricity current at the time of supplying electricity for the heater. The internal pressure of the exhaust pipe may be detected by using sensors, or may be assumed to be same as the atmospheric pressure.

When it is determined that the exhaust pipe 14 is in a water drop condensing state (i.e., YES in S12), the control process proceeds to step S13, and a water existence flag Fwe is set to "1." In the following step S14, the calculation of the amount of PM based on the PM detection voltage Vpm is prohibited, and the forcible burning of PM accumulated on the insulating substrate 32 is prohibited.

When it is determined that the water drop condensation possibility in the exhaust pipe 14 is decreased (i.e., NO in S12), the control process proceeds to step S15. The process after step S15 is to determine whether or not the PM sensor 17 is actually free of water attached thereto (i.e., whether no water exists in the exhaust passage), even though the determination based on the saturated steam pressure indicates that the possibility of water drop condensation in the exhaust passage is diminished.

In step S15, the PM detection voltage Vpm is acquired, and it is determined whether the water is attached to the PM detector 34 based on the acquired PM detection voltage Vpm in step S16. In such case, decreasing change of the resistance values of the PM detector 34 is detected so as to detect the water (e.g., water drop) attachment to the pair of detection electrodes 36a, 36b. That is, when the PM detection voltage Vpm is in a predetermined range Vwt, the process in S16 is determined as YES. The predetermined range Vwt is defined based on the electrical resistance value of water, and the range Vwt is included within a range of the resistance values that can be output from the PM detector 34 when there is drop of water between the pair of detection electrodes 36a, 36b.

In the present embodiment, the PM detection voltage Vpm at the time of stopping of the engine 11 is acquired as a stop time detection value, and the predetermined range Vwt is set based on the stop time detection value. In other words, the predetermined range Vwt is defined as a sum of the stop time detection value and the voltage value corresponding to the resistance value of water. Alternatively, the PM detection voltage Vpm is acquired as the detection value at the beginning of the current start time of the engine 11, and the predetermined range Vwt may be set based on the start time detection value.

Further, two values for the predetermined range Vwt (i.e., a maximum value and a minimum value) may be set to determine whether the PM detection voltage Vpm is included in the range Vwt. Alternatively, one predetermined value may be defined as the predetermined range Vwt, so as to determine whether the PM detection voltage Vpm is equal to or greater than the one predetermined value.

If the determination of step S16 is YES, the control process proceeds to step S13, and the water existence flag Fwe is set to "1," and, in the following step S14, a control performed by utilizing the actual PM emission amount that is calculated based on the detection signal of the PM sensor 17 is prohibited, and the forcible burning of the PM accumulated on the insulating substrate 32 is prohibited.

On the other hand, if the determination of step S16 is NO, it is determined whether the water existence flag Fwe is set to "0" in step S17. If the determination of step S17 is YES, the control process proceeds to step S18, while the water existence flag Fwe is maintained at "0," and the process further proceeds to step S20. Further, if the determination of step S17 is NO, the control process proceeds to step S19, and it is determined whether the water attached to the PM sensor 17 has disappeared or not based on the PM detection voltage Vpm. In such case, increasing change of the resistance value of the PM detector 34 is detected thereby detecting the disappearance of water existing between the pair of detection electrodes 36a, 36b. That is, when the PM detection voltage Vpm is equal to or smaller than a threshold value Vthw, step S19 is determined as YES.

In the present embodiment, the threshold value Vthw is set based on the stop time detection value (i.e., the PM detection voltage Vpm) which is acquired at the time of stopping of the engine 11, in the same manner as the predetermined range Vwt. In such case, the threshold value Vthw is set as a substantially same voltage value as the stop time detection value. Alternatively, the PM detection voltage Vpm is acquired as the detection value at the beginning of the current start period of the engine 11, and the predetermined range Vwt may be set based on the start time detection value.

If step S19 is NO, the control process proceeds to step S13, at which the water existence flag Fwe is maintained at "1," and a control is performed by utilizing the detection value of the PM sensor 17 and the forcible burning process of PM is prohibited in step S14. On the other hand, if the determination of step S19 is YES, the control process proceeds to step S18, and the water existence flag Fwe is set to "0," and the control process proceeds to step S20.

In step S20, it is determined whether a forcible burning request is made in the PM sensor 17. In the present embodiment, based on at least one of the following four conditions (a) it is an engine start time period, (b) it is an end of engine operation, (c) the amount of PM accumulation reaches a predetermined value, or (d) the amount of total engine operation time or vehicle travel distance reaches a certain threshold value, a forcible PM burning flag Fbu is set (e.g., Fbu=1), and the forcible burning request is made. Therefore, determination in step S20 is YES, if the forcible PM burning for the PM sensor 17 is not yet performed at the present engine start time period.

If step S20 is determined as YES, the control process proceeds to step S21 to perform the forcible PM burning for the PM sensor 17. In step S21, forcible PM burning process is carried out. More practically, the heater 35 of the PM sensor 17 receives electricity supply. If the determination of step S20 is NO, the control process proceeds to step S22, and it is determined whether the forcible PM burning process for the PM sensor 17 is finished or not. If the forcible PM burning process is finished at step S22, the control process proceeds to step S23, and a control by utilizing the actual PM emission amount that is calculated based on the detection signal of the PM sensor 17 is started. More practically, a combustion state of the engine 11 is diagnosed based on the actual PM emission amount, and a fuel injection amount control, a fuel injection timing control or/and an ignition timing control of the engine 11 may be performed based on the actual PM emission amount.

Further, in case that the water existence flag Fwe is set to "0" in step S18, that is, when water is determined to exist in the exhaust pipe 14, the microcomputer 44 switches electricity supply to the heater of the A/F sensor 16 from a restriction imposed state to a restriction released state. For example, electricity supply to the heater of the A/F sensor 16 is switched from a prohibition state to an allowed state. In such case, the electricity supply to the heater of the A/F sensor 16 is started when it is determined that the water attachment has disappeared based on the PM detection voltage Vpm.

Figure 5:
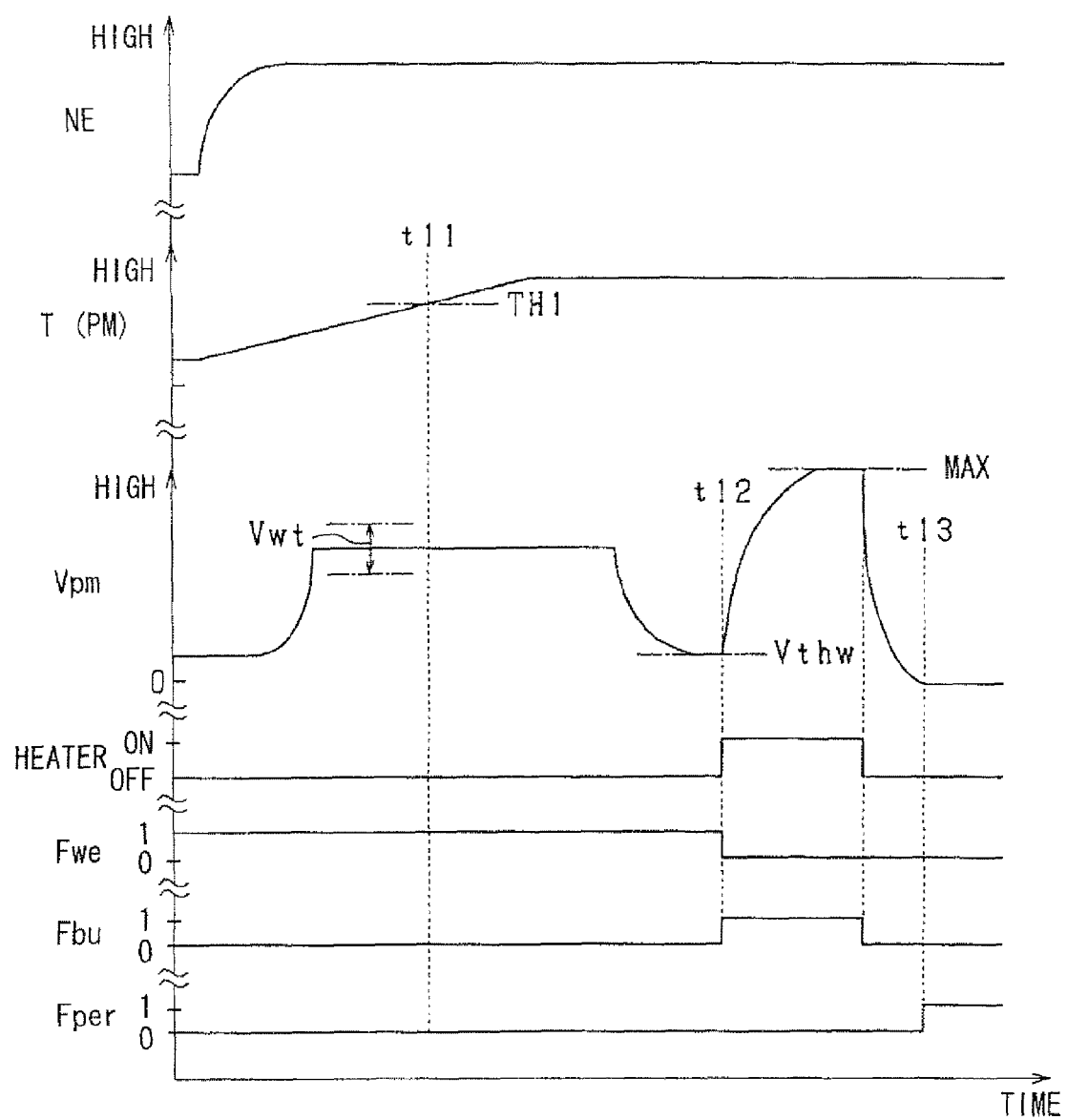
FIG. 5 is a time chart of the water attachment determination process in the embodiment of the present disclosure.

FIG. 5 is a detailed time chart to explain a water attachment determination process of the PM sensor 17 at a cold start time period of the engine 11. In FIG. 5, NE indicates the rotation speed of the engine 11, T(PM) indicates the ambient temperature of the PM sensor 17, Vpm indicates the PM detection voltage, Fwe indicates the water existence flag, Fbu indicates the forcible PM burning flag, and Fper indicates a PM measurement permission flag. For example, when water exists in the exhaust pipe, the water existence flag Fwe is set at 1; and when water does not exist in the exhaust pipe, the water existence flag Fwe is reset (Fwe=0). The PM forcible burning flag Fbu is set at 1 when the PM forcible burning is requested, and the PM forcible burning flag Fbu is reset (Fbu=0) when the PM forcible burning is not requested, for example. Furthermore, the PM measurement permission flag Fper is set at 1 when the PM measurement is permitted, and the PM measurement permission flag Fper is reset (Fper=0) when the PM measurement is not permitted, for example.

In FIG. 5, the water existence flag Fwe is set (e.g., Fwe=1) before the ambient temperature T(PM) of the PM sensor 17 reaches a predetermined value TH1 at a timing t11, and both of the forcible PM burning process and a control of the engine based on the PM detection voltage Vpm are prohibited. Further, the predetermined value TH1 is a temperature value when the internal pressure of the exhaust pipe is equal to the atmospheric pressure. That is, if the internal pressure of the exhaust pipe is one atmospheric pressure, the value TH1 is equal to 100° C. Before the timing t11, the saturated steam pressure at the ambient temperature T(PM) of the PM sensor 17 is lower than the internal pressure of the exhaust pipe 14, thereby providing an environment that easily causes water drop condensation in the inside of the exhaust pipe 14.

After the timing t11, a high temperature exhaust gas from the engine 11 raises the sensor ambient temperature T(PM), and the environment in the exhaust pipe 14 may be turned to have no water condensation. However, even after the timing t11, there is not a little chance of water attachment to the PM sensor 17, because vaporization of the water drops in the exhaust pipe 14 takes some time. Further, due to the uneven temperature distribution in the exhaust pipe 14, the environment in the exhaust pipe 14 may not be accurately determined based on the exhaust gas temperature, in terms of whether the environment no longer allows easy water condensation.

In view of such a situation, after the timing t11, while the PM detection voltage Vpm stays within the predetermined range Vwt, it is determined that water is still existing in the exhaust pipe 14, and the water existence flag Fwe is kept in a set state (e.g., Fwe=1). In such case, both of the forcible PM burning process and the control of the engine 11 based on the PM detection voltage Vpm are prohibited.

When the PM detection voltage Vpm becomes equal to or lower than the threshold value Vthw after the timing t11, the water existence flag Fwe is reset to zero at a timing t12, and a forcible PM burning flag Fbu is set (e.g., Fbu=1). In such a manner, the electricity is supplied to the heater 35, and the forcible burning of the accumulated PM is performed. In such case, the forcible PM burning flag Fbu may be set at 1, after a predetermined time elapses from the resetting of the water existence flag Fwe (Fwe=0).

The increase of the PM detection voltage Vpm after the start of electricity supply to the heater 35 is caused by the decrease of the resistance value between the electrodes due to the increase of the temperature of the accumulated PM on the PM sensor 17 (i.e., the insulating substrate 32). In other words, PM has a temperature characteristic that its resistance value decreases when its temperature increases. Therefore, when the resistance value of the PM decreases, the PM detection voltage Vpm increases to have a maximum value (MAX), and the voltage Vpm with the maximum value is continued for a predetermined time period. Then, after the forcible PM burning is performed to remove the accumulated PM, the resistance value is increased, thereby resulting in the decrease of the PM detection voltage Vpm. That is, the voltage Vpm falls to be substantially equal to 0 at a timing t13.

When the PM detection voltage Vpm becomes substantially equal to 0 after the decreasing, electricity supply to the heater 35 is turned off and the forcible PM burning flag Fbu is reset at the timing t13, based on the determination that the forcible PM burning is finished, and a PM measurement permission flag Fper is set (e.g., Fper=1). Further, the forcible PM burning flag Fbu may be reset zero when the PM detection voltage Vpm is changed to a decreasing side, and, at the same time, electricity supply to the heater 35 may be turned off. Furthermore, the PM measurement permission flag Fper may be set at 1 after a predetermined time elapses from the resetting of the forcible PM burning flag Fbu.

According to the present embodiment described in the above, the following advantageous effects are achieved.

The water attachment to the PM sensor 17 is determined based on difference values of the PM detection voltage Vpm, at a water-attached state of the insulating substrate 32 and at a water-disappeared state of the insulating substrate 32. In other words, the configuration of the sensor controller enables water existence determination for determining whether water exists in the exhaust pipe 14.

Further, when the PM detector 34 has the accumulated PM attached thereto at the engine start time, it can accurately determine whether the PM detection voltage Vpm is caused by the accumulated PM, or whether the PM detection voltage Vpm is caused by the attachment of water. This is because such determination is configured to be performed based on the comparison between the stop time detection value and the start time detection value, that is, the stop time detection value acquired as the PM detection voltage Vpm at the time of stopping of the engine 11, and the start time detection value acquired as the PM detection voltage Vpm during a predetermined period from the start of the engine 11 after previous stopping.

Furthermore, water existence in the exhaust pipe 14 (i.e., the water attachment to the PM sensor 17) can be accurately detected and water disappearance timing in the exhaust pipe 14 (i.e., the water attachment removing timing) can be appropriately determined, due to the above configuration. Furthermore, if the PM detection voltage Vpm increases and then decreases, it is determined that water in the exhaust pipe 14 has disappeared. More specifically, according to the water attachment determination by utilizing the PM detection voltage Vpm, the water disappearance is directly determined based on the detection signal from the PM sensor 17, thus the detection accuracy of water disappearance timing is improved, relative to the determination that utilizes the environmental parameters of the PM sensor 17 such as temperature, the saturated steam pressure or the like, for example.

Furthermore, because the configuration of the sensor controller of the present disclosure prohibits a control that utilizes the PM detection voltage Vpm when the water is detected in the exhaust pipe 14, an incorrect control of the PM amount can be prevented, and the control based on the amount of PM can be appropriately performed.

Furthermore, because the forcible PM burning for burning the PM accumulated on the insulating substrate 32 is prohibited when water is detected in the exhaust pipe 14, damage to the sensor element 31 is appropriately prevented.

Furthermore, the restriction on the electricity supply to the heater 35 of the A/F sensor 16 is released at a water disappearance timing from the exhaust pipe 14 when the engine 11 is started. In other words, a restriction release timing to supply electricity to the heater 35 is accurately determined, and too early release of the restriction or too late release of the restriction is prevented. In such case, a needless delay of the release of restriction of the electricity supply to the heater is prevented, thereby enabling an early activation of the A/F sensor 16. As a result, the air-fuel ratio feedback control is started much earlier, for the improvement of the exhaust purification capacity.

Other Embodiments

Although the present disclosure has been fully described in connection with preferred embodiment thereof with reference to the accompanying drawings, it is to be noted that various changes and modifications will become apparent to those skilled in the art.

For example, based on the rate of change of the PM detection voltage Vpm, water in the exhaust pipe 14 may be detected. More practically, the rate of increase of the PM detection voltage Vpm in a predetermined start period at the engine start time is calculated, and water in the exhaust pipe 14 is detected by comparing the rate of increase of the voltage Vpm with a standard increase rate calculated in advance. In other words, the rate of increase of the voltage Vpm has a relatively small value if the increase of the PM detection voltage Vpm is caused by the increased amount of PM accumulation. However, the rate of increase of the PM detection voltage Vpm has a relatively great value when water attached to the PM detector 34 at the engine start time drastically decreases the resistance value of the PM detector 34. Taking advantage of such change of the increase rate of the PM detection voltage Vpm, it can determine whether water is attached to the PM detector 34 during an engine start period.

Figure 6:
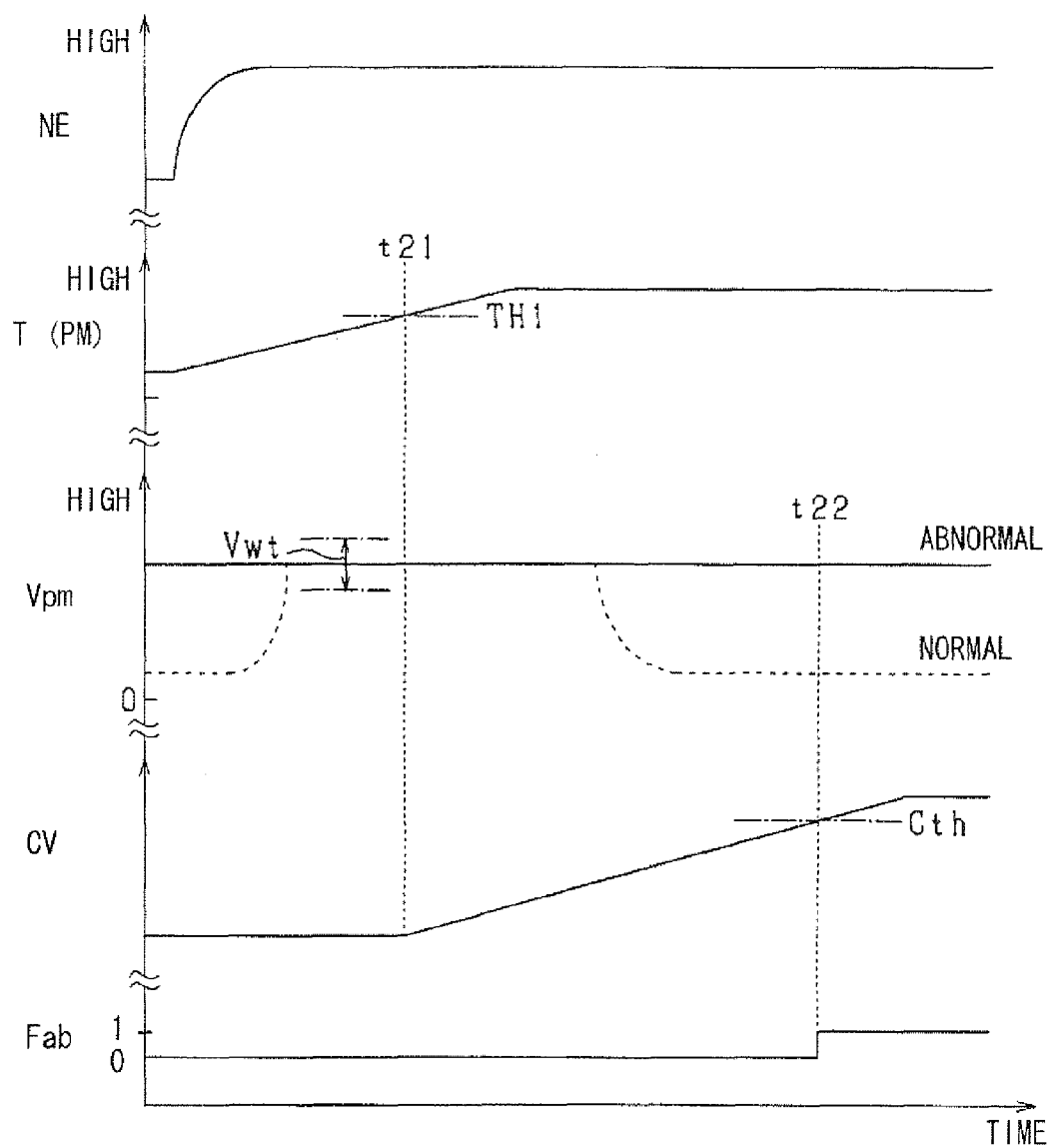
FIG. 6 is a time chart of a sensor abnormality diagnosis process in another embodiment of the present disclosure.

Further, during a predetermined start period of the engine 11, the abnormality diagnosis of the PM sensor 17 may be performed based on the duration of the PM detection voltage Vpm staying at a value that corresponds to the resistance value of water. FIG. 6 is a time chart of a sensor abnormality diagnosis process, to illustrate a situation of the engine start period. In FIG. 6, when the ambient temperature of the PM sensor 17 reaches a predetermined value TH1 at a timing t21, a count up of a water attachment detection improper counter (CV) is started in FIG. 6. If an increase of the PM detection voltage Vpm during the engine start period is due to the water attachment to the PM sensor 17, water drops on the PM sensor 17 vaporizes as the ambient temperature of the PM sensor increases, and the PM detection voltage Vpm decreases at a timing t22. In such case, it is determined that the PM sensor 17 is normal.

In contrast, if an increase of the PM detection voltage Vpm is not due to water attachment to the PM sensor 17, and, for example, is due to irremovable foreign matter such as metal pieces attached to the insulating substrate 32 of the PM sensor 17, or is due to impurities in the insulating substrate 32 causing a weak leak current, the PM detection voltage Vpm continues to stay at a high value. In such case, the water attachment detection improper counter (CV) reaches an abnormality determination value Cth at the timing t22, and the PM sensor abnormality determination flag Fab is set (e.g., Fab=1).

Furthermore, a device to determine whether there is water in the exhaust pipe 14 based on a parameter other than the PM detection voltage Vpm (e.g., temperature or saturated steam pressure) may be provided, and, the abnormality diagnosis of the PM sensor 17 may be performed based on the PM detection voltage Vpm that is detected while water existence in the exhaust pipe 14 is detected by such device. If the PM detection voltage Vpm during such period does not indicate a value corresponding to the resistance value of water, the PM sensor 17 is determined to be abnormal.

Figure 7:
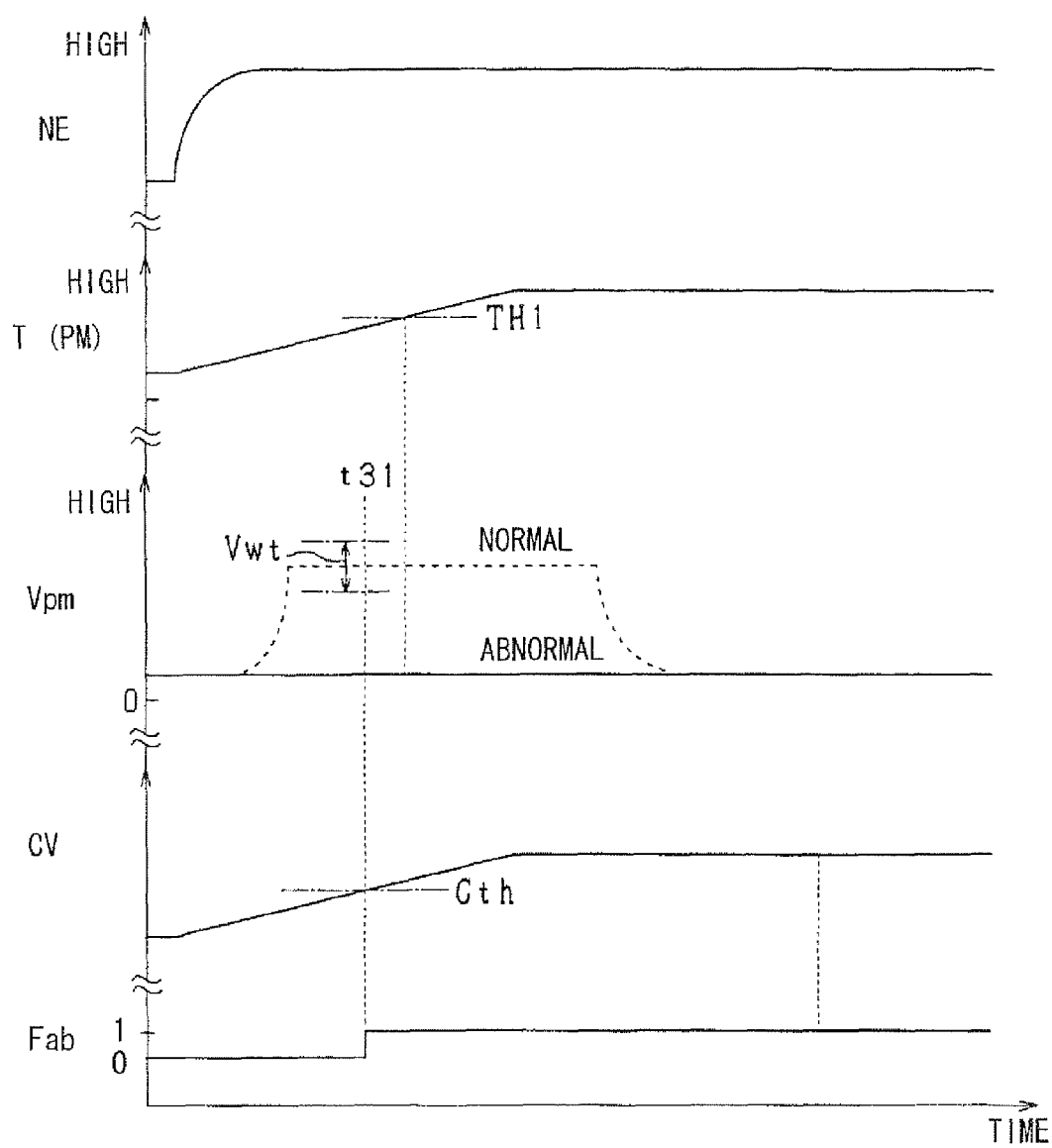
FIG. 7 is a time chart of the sensor abnormality diagnosis process in another embodiment of the present disclosure.

FIG. 7 is a time chart of the sensor abnormality diagnosis process to more practically explain how such abnormality diagnosis is performed, and the time chart illustrates a situation during the engine start period. When the count up of the water attachment detection improper counter (CV) is started at the time of starting the engine 11 as shown in FIG. 7, the PM detection voltage Vpm is acquired at a timing t31 when the counter value (CV) reaches the threshold Cth. If the PM detection voltage Vpm is small and not falls within the predetermined range Vwt, the PM sensor 17 is determined as abnormal, and the PM sensor abnormality determination flag Fab is set at 1, for example.

The abnormal diagnosis of the PM sensor 17 may be carried out based on the PM detection voltage Vpm, and, during a predetermined cold start period at the engine start time, the abnormality diagnosis of the PM sensor 17 may be prohibited. The above modification is due to the following reasons. That is, when water is attached to the PM sensor 17, the resistance value between the pair of detection electrodes 36a, 36b decreases even if it is just after the removal of PM by the forcible PM burning, and thereby it is possible to cause the PM detection voltage Vpm to exceed the abnormality determination value. Alternatively, the rate of the increase of the PM detection voltage Vpm may be fast enough to be determined as abnormal. However, the increase of the PM detection voltage Vpm may be only temporary, and the voltage Vpm may come back to the normal range after the warm-up of the engine 11, which leads to a high temperature condition in the inside of the exhaust pipe 14, and which vaporizes the attached water. In such case, the PM sensor 17 is no longer in the abnormal condition. Therefore, such recoverable and temporal abnormality should not be determined and diagnosed as irrecoverable (i.e., real) abnormality. Therefore, as described above, during the cold start period of the engine, the abnormality diagnoses based on the PM detection voltage Vpm can be prohibited.

When it is determined that water is attached to the PM sensor 17, electricity supply to the heater 35 may be controlled to have a smaller electricity amount relative to the electricity amount for forcible PM burning. In such configuration, the damage of the sensor 17 due to a quick heating is prevented, while vaporizing the attached water by using the heater 35 in a shortest possible time.

The forcible burning of PM may be performed at an end of the engine operation, and the PM accumulation amount on the PM detector 34 at the subsequent engine start time may be set at zero, or may be set substantially to zero. In such configuration, as the PM amount is equal to zero at the engine start time, electricity will not be conducted between the detection electrodes due to the accumulation of PM, thereby making the voltage Vpm being equal to 0 (V). Therefore, water attachment on the insulating substrate 32 during the engine start period can be easily detected based on the PM detection voltage Vpm.

Further, the forcible burning of PM may be configured to be performed before condensation/attachment of water at the engine start time, in addition to that the forcible burning of PM at the end of the engine operation.

The catalyst 15 may be provided as an exhaust gas treatment apparatus equipped with a heater. More practically, the catalyst 15 may have a heater in or on a carrier. In such case, water existence in the exhaust pipe 14 is determined based on a detection signal (i.e., the PM detection voltage Vpm) from the PM sensor 17, and electricity supply to the heater is either allowed or prohibited based on the result of the above determination.

Foreign matter attached to the insulating substrate 32 of the PM sensor 17 may be identified based on the change of the PM detection voltage Vpm. More practically, when conductive material such as a piece of metal or water falls on the insulating substrate 32, the PM detection voltage Vpm can change, and the changing behavior of the PM detection voltage Vpm varies depending on the foreign matter attached to the insulating substrate 32. Therefore, the change of the PM detection voltage Vpm or its changing behavior may be pre-identified for material to material, and the comparison between those changes against a standard value enables identification of what the attached foreign matter is based on the PM detection voltage Vpm.

The signal output circuit utilizing the voltage-dividing circuit 40 shown in FIG. 3 may have a different configuration. For example, the positions of the PM detector 34 and the shunt resistor 42 in the voltage-dividing circuit 40 may be reversed to have the PM detector 34 on the low side and the shunt resistor 42 on the high side. In such configuration, the PM detection voltage Vpm is calculated by using the following equation (2).

$$Vpm = 5V \times Rpm/(Rs + Rpm) \qquad (2)$$

In the above equation (2), Rpm is a resistance value of the PM detector 34, and Rs is a resistance value of the shunt resistor 42 (e.g., 5 kΩ).

In the above configuration, the heater 35 is disposed on the insulating substrate 32 in an integrated body. However, the temperature of the ambient gas around the PM sensor 17 (e.g., the exhaust gas from the engine) may be increased to a burning temperature of PM. In such case, the temperature of the exhaust gas from the engine 11 may be increased by the engine combustion control, or other heating devices (e.g., another heater) may be disposed in the exhaust pipe.

A PM filter to collect PM may be disposed in an engine exhaust pipe, and at least one of a downstream side or an upstream side of the PM filter may have the PM sensor, for determining a PM filter refresh timing based on the PM sensor detection value. Further, breakdown diagnosis of the PM filter may be performed based on the PM sensor detection value.

In the above embodiments, an application of the present disclosure to a direct fuel-injection gasoline engine is exemplified. However, the sensor controller of the present disclosure may be applicable to other types of engines. For example, it may be applicable to a diesel engine (in particular, a direct fuel-injection diesel engine), and the sensor controller can be used in a PM sensor disposed in the exhaust pipe of the diesel engine. Further, PM amount detection of the present disclosure may be applicable to other types of gas, other than the exhaust gas that is explained in the present disclosure.

According to an aspect of the present disclosure, a sensor controller to be disposed in an exhaust passage 14 of an internal combustion engine 11 includes: a particulate matter detection sensor 17 that includes a pair of opposed electrodes 36a, 36b spaced from each other and disposed on an attachment portion 32 to which conductive particulate matter contained in gas of the exhaust passage is attached so as to output a detection signal corresponding to a resistance value between the pair of opposed electrodes 36a, 36b; a calculation portion (20) configured to calculate an amount of particulate matter attached to the particulate matter detection sensor 17 based on a detection value from the particulate matter detection sensor 17; and a determination portion (20) configured to determine whether water exists in the exhaust passage based on the detection value.

When the particulate matter detection sensor 17 has PM attached to the attachment portion 32, the resistance value between the opposed electrodes changes, and the detection value also changes based on the change of the resistance value. In the present disclosure, change of the resistance value due to the attachment of water on the attachment portion 32 is utilized, for the detection of water in the exhaust passage 14 based on the detection value from the particulate matter detection sensor 17. Thus, it is possible to predict behaviors of the detection value at a time of water attachment. For example, an actual detection value and a signal output range at a water attachment state are compared with each other, thereby accurately determining whether water exists on the attachment portion 32.

The determination portion may determine that water in the exhaust passage has disappeared, when the detection value of the resistance value between the pair of opposed electrodes is changed to be decreased, and then when the detection value of the resistance value is changed to be increased after being decreased.

For example, when water exists in the exhaust passage 14 at the start time of the internal combustion engine 11, the water is attached to the attachment portion 32 of the particulate matter detection sensor 17. However, the attachment of the water on the sensor 17 may be only temporary, because the exhaust passage 14 is brought to a high temperature condition due to the combustion of the fuel. In such a case, the resistance value between the pair of opposed electrodes 36a, 36b decreases due to the attachment of water, and the resistance value between the pair of opposed electrodes 36a, 36b increases due to the disappearance of water. In the present disclosure, because the determination portion determines that water in the exhaust passage 14 has disappeared, when the detection value of the resistance value between the pair of opposed electrodes 36a, 36b is changed to be decreased, and then when the detection value of the resistance value is changed to be increased after being decreased, the water in the exhaust passage can be accurately determined.

The determination portion may determine that water exists in the exhaust passage 14 based on a rate of the change of the detection value.

If attachment of PM in the exhaust on the attachment portion 32 and attachment of water in the exhaust passage on the attachment portion 32 are compared with each other, the change rate of the sensor detection value from the particulate matter detection sensor 17 is faster than the change of the sensor detection value of the former case. Therefore, the change rate of the sensor detection value from the particulate matter detection sensor 17 is used as a parameter for determining the existence of water in the exhaust passage 14.

The sensor controller may include means for removing the particulate matter attached to the attachment portion 32. In this case, the determination portion acquires a detection value in a PM-removed condition removed by the removal means, and the determination portion determines whether water exists based on the acquired detection value in the PM-removed condition. Thus, the amount of the particulate matter on the attachment portion can be considered to be equal to zero, when the water existence determination is performed. That is, the resistance value does not include the particulate matter component, by the removal of the particulate matter. Therefore, the detection of water existence can be easily and accurately performed.

In such case, the particulate-matter removed condition may include a condition in which the amount of particulate matter on the attachment portion 32 is zero, or may include a condition in which the amount of particulate matter on the attachment portion 32 is substantially equal to zero.

The sensor controller may further include means for acquiring the detection value at a time of stopping of the internal combustion engine 11 as a stop time detection value, and means for acquiring the detection value at a start time period subsequent to a stopping of the internal combustion engine 11, as a start time detection value. In this case, the determination portion determines whether water exists in the exhaust passage by comparing the stop time detection value with the start time detection value.

At the time of the stopping of the internal combustion engine 11, the detection signal of the particulate matter detection sensor 17 appropriately reflects the amount of attachment of the particulate matter, because it is not necessary to consider the influence of water on the resistance value between the opposing electrodes 36a, 36b. Further, the amount of attachment of the particulate matter at the time of stopping of the engine 11 and the amount of attachment of the particulate matter at the subsequent start time of the engine 11 should be the same, because no new particulate matter is attached to the attachment portion 32 during the time of engine stopping to the subsequent start time. In other words, if the start time detection signal is different from the stop time detection signal, it may determine the attachment of water. According to the above configuration, a water attachment determination can be carried out taking into account the amount of attachment of the particulate matter at the engine start time of the internal combustion engine 11.

When the determination portion determines that water exists in the exhaust passage 14, the calculation portion may prohibit calculation of the amount of particulate matter attached to the particulate matter detection sensor.

Furthermore, a heater 35 may be disposed to heat the attachment portion 32 so as to burn particulate matter attached to the attachment portion 32. In this case, when the determination portion determines that water exists in the exhaust passage 14, the heating of the attachment portion 32 by using the heater 35 is restricted. In addition, how "restriction on heating of the attachment portion 32" is performed may include (a) prohibition of heating of the attachment portion 32 by the heater 35, and (b) restriction on supply of electricity to the heater 35 or the like, for example.

For example, the sensor controller may be used for an exhaust gas treatment system. In this case, the exhaust gas treatment system may be provided with at least one of a heater-equipped exhaust sensor and a heater-equipped exhaust gas treatment device disposed in the exhaust passage 14, and a heater control portion that is configured to reduce an electricity supply to a heater in the at least one of the heater-equipped exhaust sensor and the heater-equipped exhaust gas treatment device based on a determination result of the determination portion. Thus, it is possible to perform an early start of feedback control of the air-fuel ratio, for the improvement of the exhaust purification capacity.

Such changes, modifications, and summarized schemes are to be understood as being within the scope of the present disclosure as defined by appended claims.

What is claimed is:

1. A sensor controller to be disposed in an exhaust passage of an internal combustion engine, the sensor controller comprising:
   a particulate matter detection sensor that includes a pair of opposed electrodes spaced from each other and disposed on an attachment portion to which conductive particulate matter contained in gas of the exhaust passage is attached, the particulate matter detection sensor being disposed to output a detection signal corresponding to a resistance value between the pair of opposed electrodes;
   a calculation portion configured to calculate an amount of particulate matter attached to the particulate matter detection sensor, based on a detection value from the particulate matter detection sensor; and
   a determination portion configured to determine whether water exists in the exhaust passage based on the detection value, wherein
   the determination portion determines that water exists in the exhaust passage based on a rate of the change of the detection value during a time period from a start of the internal combustion engine.

2. The sensor controller of claim 1, wherein if the detection value of the resistance value between the pair of opposed electrodes is decreased and then increased, then the determination portion determines that water in the exhaust passage has been removed.

3. The sensor controller of claim 1, further comprising:
   means for removing the particulate matter attached to the attachment portion, wherein
   the determination portion acquires a detection value in a PM-removed condition removed by the removal means, and
   the determination portion determines whether water exists based on the acquired detection value in the PM-removed condition.

4. The sensor controller of claim 3, further comprising:
   means for acquiring the detection value at a time of stopping of the internal combustion engine as a stop time detection value after the particulate matter is removed; and
   means for acquiring the detection value at a start time period subsequent to a stopping of the internal combustion engine, as a start time detection value, wherein
   the determination portion determines whether water exists in the exhaust passage by comparing the stop time detection value with the start time detection value.

5. The sensor controller of claim 1, wherein
   when the determination portion determines that water exists in the exhaust passage, the calculation portion prohibits calculation of the amount of particulate matter attached to the particulate matter detection sensor.

6. An exhaust gas treatment system comprising:
   the sensor controller according to claim 1;
   at least one of a heater-equipped exhaust sensor and a heater-equipped exhaust gas treatment device disposed in the exhaust passage; and
   a heater control portion configured to reduce an electricity supply to a heater in the at least one of the heater-equipped exhaust sensor and the heater-equipped exhaust gas treatment device, based on a determination result of the determination portion.

7. The sensor controller of claim 1, wherein
   the time period is a time from the start of the internal combustion engine to an end of warming-up of the internal combustion engine.

8. The sensor controller of claim 1, wherein
   the time period is a time from the start of the internal combustion engine to a time at which a coolant temperature of the internal combustion engine is increased to a predetermined value.

9. A sensor controller to be disposed in an exhaust passage of an internal combustion engine, the sensor controller comprising:
   a particulate matter detection sensor that includes a pair of opposed electrodes spaced from each other and disposed on an attachment portion to which conductive particulate matter contained in gas of the exhaust passage is attached, the particulate matter detection sensor being disposed to output a detection signal corresponding to a resistance value between the pair of opposed electrodes;
   a calculation portion configured to calculate an amount of particulate matter attached to the particulate matter detection sensor, based on a detection value from the particulate matter detection sensor;
   a determination portion configured to determine whether water exists in the exhaust passage based on the detection value; and
   a heater disposed to heat the attachment portion so as to burn particulate matter attached to the attachment portion, wherein
   when the determination portion determines that water exists in the exhaust passage, the heating of the attachment portion by using the heater is restricted.

* * * * *